United States Patent [19]

Saari

[11] Patent Number: 4,892,951

[45] Date of Patent: * Jan. 9, 1990

[54] DERIVATIVES OF 3-NITROPYRIDINES USEFUL AS ADJUNCTS TO RADIATION THERAPY

[75] Inventor: Walfred S. Saari, Lansdale, Pa.

[73] Assignee: Merck & Co., Inc., Rahway, N.J.

[*] Notice: The portion of the term of this patent subsequent to Sep. 2, 2003 has been disclaimed.

[21] Appl. No.: 273,122

[22] Filed: Nov. 17, 1988

Related U.S. Application Data

[63] Continuation of Ser. No. 885,513, Jun. 10, 1986, abandoned, which is a continuation of Ser. No. 716,885, Mar. 27, 1985, abandoned.

[51] Int. Cl.$^4$ ............................................. C07D 213/76
[52] U.S. Cl. .................................................... 546/307
[58] Field of Search ......................... 514/352; 546/307

[56] References Cited

U.S. PATENT DOCUMENTS 4,443,458  4/1984  Hartman ............................ 546/307
4,609,659  9/1986  Hartman ............................ 514/255

FOREIGN PATENT DOCUMENTS 0111151  6/1984  European Pat. Off. .

OTHER PUBLICATIONS

Olive, P. L. Cancer Research 39 pp. 4512–4515 (Nov. 1979).

Israel, M. et al. J. Med. Chem. (1973) vol. 6 No. 5 pp. 520–524.

Primary Examiner—Jane T. Fan
Attorney, Agent, or Firm—Robert J. North; Joseph F. DiPrima

[57] ABSTRACT

Substituted 3-nitropyridines are disclosed to have activity in increasing the sensitivity of hypoxic tumor cells to therapeutic radiation. Also disclosed are methods of preparing such compounds by amination of the corresponding chloro-3-nitropyridine with 2,3-dihydroxypropylamine and pharmaceutical compositions including such compounds.

5 Claims, No Drawings

DERIVATIVES OF 3-NITROPYRIDINES USEFUL AS ADJUNCTS TO RADIATION THERAPY

BACKGROUND OF THE INVENTION

This invention relates to substituted 3-nitropyridine compounds used as sensitizers of hypoxic tumor cells to therapeutic radiation. It also relates to the process of preparing such compounds by aminating chloro-3-nitropyridines to produce the substituted 3-nitropyridines.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds of the present invention are effective radiation sensitizers, and are believed to have a more favorable therapeutic ratio.

DETAILED DESCRIPTION OF THE INVENTION

The compositions of the present invention are nitropyridine compounds of the formula

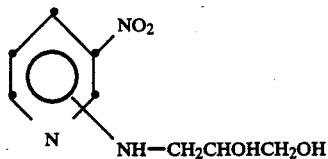

I wherein the NHCH$_2$CHOHCH$_2$OH group is attached at position 2, 4, or 6 of the pyridine ring.

The substituted nitropyridine compounds of the present invention are prepared in the following manner:

A (2,4 or 6)-chloro-3-nitropyridine of the formula:

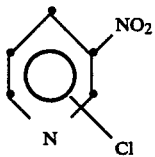

in a suitable solvent such as a lower aliphatic alcohol, or a polar aprotic solvent such as dimethylformamide, dimethylsulfoxide, or others such as tetrahydrofuran, glyme, diglyme, tetramethylurea, chloroform, or methylene chloride is treated with the selected amine reactant of the formula H$_2$NCH$_2$CHOHCH$_2$OH, in the presence of sufficient base to neutralize the hydrogen chloride formed. The reaction temperature is not critical and may vary from 0°–100° C., preferably from about 0°–25° C. for a period of from 1–24 hours.

Suitable bases employed to neutralize the hydrogen chloride formed are tertiary amines such as triethylamine and pyridine. If desired, the neutralizing base may be supplied by using excess amine reactant. Inorganic bases such as alkali metal bicarbonates, carbonates and hydroxides may also be employed.

The product is recovered in substantially pure form by removal of solvent by evaporation under reduced pressure and the residue containing the product is chromatographed and crystallized from suitable solvents.

The method of treatment of human patients or domestic animals undergoing radiation treatment of malignant disease processes employs the compounds of the present invention in pharmaceutical compositions that are administered orally or intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

EXAMPLE 1

4-(2,3-Dihydroxy-1-propylamino)-3-nitropyridine

A solution of 4-chloro-3-nitropyridine (1.1 g, 6.94 mmol) and 3-amino-1,2-propanediol (1.22 g, 13.4 mmol) in isopropanol (50 ml) was stirred at 20°–25° C. for 20 hours and then concentrated under reduced pressure. Flash chromatography of the residue over silica gel and elution with 10% MeOH-90% CHCl$_3$ gave pure 4-(2,3-dihydroxy-1-propylamino)-3-nitropyridine (500 mg, 33.8%). An analytically pure sample, m.p. 131°–35° C., was obtained upon recrystallization from MeOH-EtOAc-hexane.

EXAMPLE 2

2-(2,3-Dihydroxy-1-propylamino)-3-nitropyridine

A solution of 2-chloro-3-nitropyridine (3.22 g, 20.3 mmol), 3-amino-1,2-propanediol (1.85 g, 20.3 mmol) and triethylamine (2.05 g, 20.3 mmol) in isopropanol (80 mL) was stirred at 20°–25° C. for 18 hours and then at reflux for 6 hours. After concentrating under reduced pressure, the residue was flash chromatographed over silica gel. Elution with 5% MeOH-95% CHCl$_3$ and recrystallization from EtOAc-hexane afforded analytically pure product (2.64 g, 61%), m.p. 95.5°–98.0° C.

EXAMPLE 3

The procedure of Example 2 was repeated using 3-nitro-6-chloropyridine in place of 2-chloro-3-nitropyridine to give 6-(2,3-dihydroxy-1-propylamino)-3-nitropyridine.

What is claimed is:

1. A method for enhancing the therapeutic effect of radiation which comprises administering to a patient in need of such radiation treatment an effective amount of a 3-nitropyridine compound of the formula

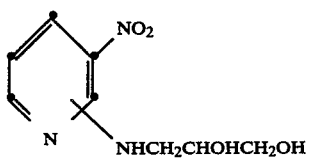

wherein the NHCH$_2$CHOHCH$_2$OH substitutent is attached at position 2, 4 or 6.

2. A pharmaceutical composition for enhancing the therapeutic effect of radiation which contains an effective amount of a compound defined in claim 1 and a non-toxic pharmaceutically acceptable carrier.

3. The method according to claim 1 in which the compound is 4-(2,3-dihydroxy-1-propylamino)-3-nitropyridine.

4. The method according to claim 1 in which the compound is 2-(2,3-dihydroxy-1-propylamino)-3-nitropyridine.

5. The compound: 6-(2,3-dihydroxy-1-propylamino)-3-nitropyridine.

* * * * *